United States Patent [19]

Rosenberg

[11] 4,434,792
[45] Mar. 6, 1984

[54] ADJUSTABLE ABDUCTION DEVICE FOR TREATMENT OF METATARSUS ADDUCTUS

[76] Inventor: Steven L. Rosenberg, 2901 Wilshire Blvd., Ste. 345, Santa Monica, Calif. 90403

[21] Appl. No.: 359,724

[22] Filed: Mar. 19, 1982

[51] Int. Cl.³ .............................................. A61F 3/00
[52] U.S. Cl. .................................. 128/80 R; 128/583
[58] Field of Search ................ 128/81 R, 80 R, 581, 128/583

[56] References Cited

U.S. PATENT DOCUMENTS

| 1,167,019 | 1/1916 | Reed | 128/81 R |
| 2,734,285 | 2/1956 | Levitt | 128/581 |
| 3,308,829 | 3/1967 | Edwards | 128/583 |

FOREIGN PATENT DOCUMENTS 369381 2/1923 Fed. Rep. of Germany .... 128/81 R

*Primary Examiner*—John D. Yasko
*Attorney, Agent, or Firm*—Townsend and Townsend

[57] ABSTRACT

An adjustable abduction shoe for treatment of metatarsus adductus includes an adjustable splint and heel wedge. The splint is disposed for abduction of the first metatarsal-phalangeal joint of the foot, and the wedge is disposed to prevent collapse of the midtarsal joint due to pressure. A specific embodiment is a rigid metal support bracket mounted to a shoe with one face along the exterior medial margin and transversing the vamp-/quarter seam. A splint consisting of a rigid arm, preferably a spring steel plate, is secured to the posterior end of the bracket and extends along the interior medial margin of the shoe at least as far as the first metatarsal-phalangeal joint, i.e., adjacent the big toe. Means are provided for continuously adjusting the displacement of the unattached end of the rigid arm laterally at the first metatarsal-phalangeal joint. A convex shaped pad is mounted at the heel to form a varus wedge.

4 Claims, 6 Drawing Figures

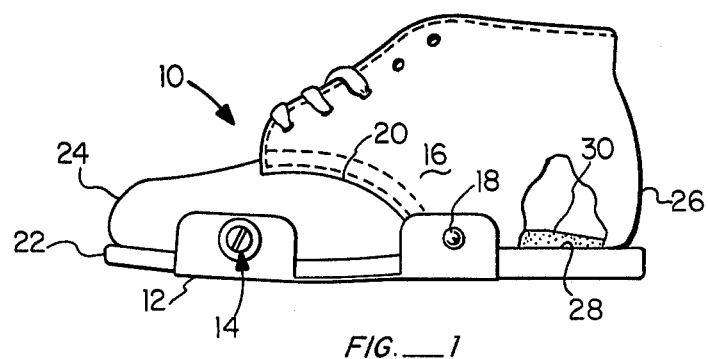
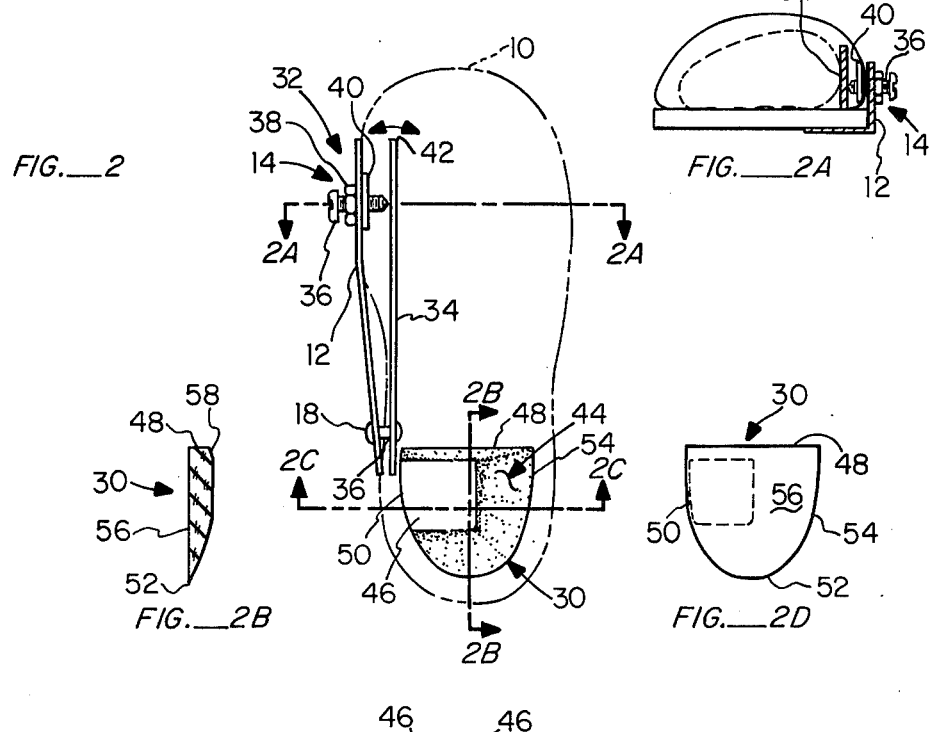

ADJUSTABLE ABDUCTION DEVICE FOR TREATMENT OF METATARSUS ADDUCTUS

BACKGROUND OF THE INVENTION

1. Field of the Invention

The present invention relates to corrective shoes, and more particularly it relates to a corrective shoe having a laterally adjustable plate along the medial margin adjacent the big toe and a varus wedge at the heel for treatment of metatarsus adductus, or skew foot. Skew foot is a common congenital foot deformity defined as a condition where the metatarsals are directed inward in relation to the lesser tarsus of the foot, i.e., the front portion of a foot tends to be medially curved.

The congenital foot deformity metatarsus adductus, or skew foot, can be corrected relatively easily, if it is not severe, during the early years of life. A common technique for reducing the deformity is to employ reverse last shoes or pronator shoes, a night splint, such as the Dennis Brown Bar or Ganley Splint, or to use a normal last shoe with an abduction strap. Reverse last shoes are the least optimal of solutions because the pressure is neither constant nor accurately applied during the abduction-based treatment, and reverse last shoes tend to cause the heel joint to collapse. Abduction strap shoes are only incrementally adjustable and may place pressure on the midtarsal joints from undesired directions and do not provide clearly defined correction.

What is needed is a corrective shoe to accurately and adjustably apply medial pressure, particularly while preventing the midtarsal joint from collapsing.

2. Description of the Prior Art

U.S. Pat. No. 3,308,829 to C. A. Edwards describes a corrective shoe with an abduction strap across the metatarsal-phalangeal joint. This patent is believed to disclose the closest known art for correction of metatarsus adductus.

U.S. Pat. No. 1,945,688 to Howell describes a shoe having screw adjustable arch support. It represents one example of adjustable spring tensioning devices on the shoe. No such spring tensioning devices are known to the inventor for medially or laterally shaping the interior envelope of a shoe.

SUMMARY OF THE INVENTION

An adjustable abduction shoe for treatment of metatarsus adducts includes an adjustable splint and heel wedge. The splint is disposed for abduction of the first metatarsal-phalangeal joint of the foot, and the heel wedge is disposed to prevent collapse of the midtarsal joint due to pressure. A specific embodiment is a rigid metal support bracket mounted to a shoe with one face along the exterior medial margin and transversing the vamp/quarter seam. A splint consisting of a rigid arm, preferably a spring steel plate, is secured to the posterior end of the bracket and extends along the interior medial margin of the shoe at least as far as the first metatarsal-phalangeal joint, i.e., adjacent the big toe. Means are provided for adjusting the displacement of the unattached end of the rigid arm laterally at the first metatarsal-phalangeal joint. A uniquely shaped pad is mounted at the heel to form a varus wedge.

It is an object of this invention to provide a continually adjustable abduction shoe for treatment of metatarsus adductus. It is a further object of the invention to provide a shoe for correction of metatarsus adductus which prevents collapse of the midtarsal joint during abduction.

These and other objects of the invention will be apparent upon reference to the following detailed description taken in connection with the accompanying drawings.

BRIEF DESCRIPTION OF THE DRAWINGS

FIG. 1 is a side elevational view of the medial portion of one embodiment of the shoe according to the invention.

FIG. 2 is a top view of an abduction device and a varus wedge showing placement in a shoe.

FIG. 2A is a cross-sectional view of a shoe along lines 2A—2A of FIG. 2.

FIG. 2B is a cross-sectional view of a varus wedge along lines 2B—2B of FIG. 2.

FIG. 2C is a cross-sectional view of a varus wedge along lines 2C—2C of FIG. 2.

FIG. 2D is a bottom view of a varus wedge according to the invention.

DESCRIPTION OF SPECIFIC EMBODIMENTS

In FIG. 1, a corrective shoe 10 according to the invention comprises a support bracket 12 with an adjustment mechanism 14 attached to the medial side 16 by means of at least one rivet 18. The shoe has a medial vamp/quarter seam 20, a sole 22, a toe end 24, a heel end 26, an innersole 28 and a varus wedge 30, the varus wedge 30 being mounted to the innersole 28 adjacent the heel end 26. Turning to FIG. 2, the abduction mechanism 32 according to the invention is shown as mounted to the shoe 10. The support bracket 12 and adjustment device 14 are attached to a rigid resilient plate 34. At the posterior end of the support bracket 12, the plate 34 is secured to the bracket 12 by rivet 18 through an opening 36 in the medial side 16. The adjustment device 14 comprises a threaded screw 36, a lock nut 38 mounted on the threaded screw 36 medially exterior of the bracket 12 which is passed through a hole in the bracket 12 and the medial side of the shoe 10 through a threaded plate 40 mounted on the interior medial side of the shoe 10. The plate 40 may be a backing plate for a nut. The purpose of the plate is to absorb the force of the big toe pushing against the rigid resilient plate 34 on the adjustment mechanism 14 along the interior of the shoe. Alternatively, the bracket 12 may be secured to the sole of the shoe with one face disposed at right angles to the secured face, for example, as shown in FIG. 2A.

The resilient plate 34 extends from its secured position by rivet 18 posterior of the medial last vamp/quarter seam 20 (FIG. 1) anterior along the medial margin of the shoe 10 to at least the position of the first metatarsal-phalangeal joint, that is, to the joint at the ball of the foot with the big toe. The plate 34 is laterally displaceable at its free end 42 in response to adjustment of the threaded screw 36. This plate is operative to abduct the foot under constant but adjustable pressure to correct metatarsus adductus.

Turning to FIGS. 2B, 2C and 2D in connection with FIG. 2, the details of the pad 30 are shown. The pad 30 comprises a top face 44 (FIG. 2) having a region of maximum thickness 46 closest to the anterior edge 48 and along the medial edge 50. The pad is tapered at a slope as much as forty-five degrees along the lateral and distal axes from the maximum thickness region to the posterior edge 52 and lateral edge 54, which are regions of minimal thickness, i.e., a fairly narrow edge forming a wedge in cross section along each of these axes (FIGS. 2B and 2C). The bottom face 56 conforms to the shape of the innersole 28 (FIG. 1). The interior edge 48 also has a slightly tapered region 58. The pad 30 thus forms a varus wedge which provides tri-plane control of the rear foot at the heel inhibiting collapse of the midtarsal joint of the foot when under abduction pressure. It specifically inhibits planar flexion and abduction of the talus bone and eversion of the calcaneous bone. The pad 30 may be of hard rubber or like material, including synthetic cork.

The plate 34 is preferably of resilient spring steel whose secured end is sufficiently compressed against the opposing bracket face adjacent the rivet 18 through the side of the shoe 10 to bias the arm 34 against the tip of the adjustment screw 36. Thus the adjustment screw 36 provides positive lateral displacement. The locking nut 38 inhibits the adjustment screw from loosening so that the abduction position can be set accurately.

The invention has now been explained with reference to specific embodiments. Other embodiments will be apparent to those of ordinary skill in the art. The invention has particular application in the treatment of metatarsus adductus in its various forms including both slight deformity and major deformity, where for example a cast is employed for initial therapy. The invention may be used after cast removal, to augment other forms of treatment, or independently without other forms of treatment as dictated by a practitioner. Therefore, it is not intended that this invention be limited, except as indicated by the appended claims.

I claim:

1. A therapeutic device for treatment of metatarsus adductus comprising:
    a shoe with a sole, an innersole, a heel end, a toe end, a medial side, a lateral side and a medial vamp-/quarter last seam;
    a support bracket rigidly secured to said medial side;
    means attached to said support bracket at a position anterior of said last seam, adjacent said toe end, and laterally of said medial side, for abducting a foot at the first metatarsal-phalangeal joint, said abducting means being laterally adjustable from the external medial side of said shoe, wherein said abducting means comprises a rigid resilient plate and an adjusting screw, said plate being secured to said bracket at a position posterior of said last seam, said adjusting screw being threadably attached to said bracket anterior of said last seam, said plate abutting to said screw and being laterally movable at its unsecured end in response to advancement of said adjusting screw; and
    means disposed to said heel end for supporting a heel of said foot in a manner to prevent the metatarsal foot joint from collapsing as the forefoot is abducted, wherein said heel supporting means comprises a pad, said pad having a top face, said top face having a region of maximum thickness closest to anterior and medial edges of said pad and having regions of minimum thickness along lateral and posterior edges of said pad thereby to form a varus wedge.

2. The device according to claim 1 wherein said top face of said pad is further tapered along the anterior margin of said pad.

3. The device according to claim 1 wherein said plate is a spring steel splint riveted to said bracket at said posterior position, wherein said plate extends along said medial last at least to said anterior position of said bracket.

4. The device according to claim 3 wherein said plate is secured to said shoe at a position exterior of said medial last and wherein said splint is secured to said bracket interior of said medial last in said shoe.

* * * * *